United States Patent
Livorsi

(10) Patent No.: US 7,947,862 B2
(45) Date of Patent: May 24, 2011

(54) LIMB STABILIZING SYSTEM FOR ARTHROPLASTY

(75) Inventor: Carl F. Livorsi, Lakeville, MA (US)

(73) Assignee: Depuy Products, Inc., Warsaw, IN (US)

( * ) Notice: Subject to any disclaimer, the term of this patent is extended or adjusted under 35 U.S.C. 154(b) by 406 days.

(21) Appl. No.: 11/926,844

(22) Filed: Oct. 29, 2007

(65) Prior Publication Data

US 2008/0132818 A1 Jun. 5, 2008

Related U.S. Application Data

(60) Provisional application No. 60/863,694, filed on Oct. 31, 2006, provisional application No. 60/863,711, filed on Oct. 31, 2006.

(51) Int. Cl.
- *A61F 13/00* (2006.01)
- *A61F 5/00* (2006.01)
- *A61F 5/37* (2006.01)
- *A61G 15/00* (2006.01)
- *A47B 7/00* (2006.01)

(52) U.S. Cl. .............. 602/42; 602/5; 602/23; 602/26; 602/28; 128/845; 128/882; 5/624

(58) Field of Classification Search .............. 602/5, 6, 602/23, 26, 28, 29, 16; 128/845, 846, 869, 128/882; 5/600, 621, 648, 601, 608, 610, 5/612, 623, 624, 650, 651, 646, 647, 937

See application file for complete search history.

(56) References Cited

U.S. PATENT DOCUMENTS

| | | | |
|---|---|---|---|
| 1,279,803 A | 9/1918 | Watson | |
| 3,762,404 A | 10/1973 | Sakita | |
| 3,858,578 A | 1/1975 | Milo | |
| 4,106,499 A * | 8/1978 | Ueda | 600/499 |
| 4,373,709 A | 2/1983 | Whitt | |
| 4,407,277 A | 10/1983 | Ellison | |
| 4,457,300 A | 7/1984 | Budde | |
| 4,545,573 A | 10/1985 | Murphy | |
| 4,615,516 A * | 10/1986 | Stulberg et al. | 5/650 |

(Continued)

FOREIGN PATENT DOCUMENTS

EP 0677274 A2 2/1995

(Continued)

OTHER PUBLICATIONS

Codman® Retractors Self-Retaining, Greenberg, dated prior to Oct. 31, 2006—2 pgs.

*Primary Examiner* — Michael Brown
*Assistant Examiner* — Ophelia Hawthorne

(57) ABSTRACT

An intraoperative leg stabilizing system has a platform with a slidable brace received in a longitudinal groove. The slidable brace supports the patient's foot. The platform also has an outrigger that pivots about a base in the platform. The outrigger can pivot up to a desired orientation. The longitudinal position of the slidable brace and the orientation of the outrigger can be fixed through locking mechanisms. The system includes a support belt that can be wrapped around the patient's thigh and then connected to the outrigger. The combination of components allows the patient's leg to be stabilized in a desired position and degree of flexion during knee arthroplasty, and to be easily released when desired for evaluation of the patient's leg in extension.

20 Claims, 8 Drawing Sheets

U.S. PATENT DOCUMENTS

| | | | |
|---|---|---|---|
| 5,007,912 A | 4/1991 | Albrektsson | |
| 5,010,900 A * | 4/1991 | Auchinleck et al. | 128/855 |
| 5,063,918 A * | 11/1991 | Guhl | 602/40 |
| 5,085,214 A | 2/1992 | Barrett | |
| 5,154,717 A | 10/1992 | Matsen et al. | |
| 5,290,220 A * | 3/1994 | Guhl | 602/33 |
| 5,569,176 A | 10/1996 | Graham | |
| 5,616,146 A | 4/1997 | Murray | |
| 5,906,586 A | 5/1999 | Graham | |
| 5,950,628 A | 9/1999 | Dunfee | |
| 5,954,638 A | 9/1999 | Spranza | |
| 6,066,107 A | 5/2000 | Habermeyer | |
| 6,071,295 A | 6/2000 | Takahashi | |
| 6,210,325 B1 | 4/2001 | Bartie et al. | |
| 6,308,353 B1 | 10/2001 | Van Steenburg | |
| 6,478,799 B1 | 11/2002 | Williamson | |
| 6,551,325 B2 | 4/2003 | Neubauer et al. | |
| 6,626,830 B1 | 9/2003 | Califiore et al. | |
| 6,882,878 B2 | 4/2005 | Schmit et al. | |
| 6,964,073 B1 | 11/2005 | Curry | |
| 7,294,104 B2 | 11/2007 | Person | |
| 7,458,977 B2 | 12/2008 | McGinley et al. | |
| 7,476,199 B2 | 1/2009 | Spence et al. | |
| 2002/0133162 A1 | 9/2002 | Axelson et al. | |
| 2002/0133163 A1 | 9/2002 | Axelson et al. | |
| 2005/0216032 A1* | 9/2005 | Hayden | 606/130 |
| 2006/0100562 A1* | 5/2006 | Pamplin | 602/32 |
| 2007/0100346 A1 | 5/2007 | Wyss et al. | |
| 2007/0123896 A1 | 5/2007 | Wyss et al. | |

FOREIGN PATENT DOCUMENTS

| | | |
|---|---|---|
| EP | 0677274 A3 | 2/1995 |
| WO | WO 02/07612 A1 | 1/2002 |
| WO | WO 2005/087116 A2 | 9/2005 |

* cited by examiner

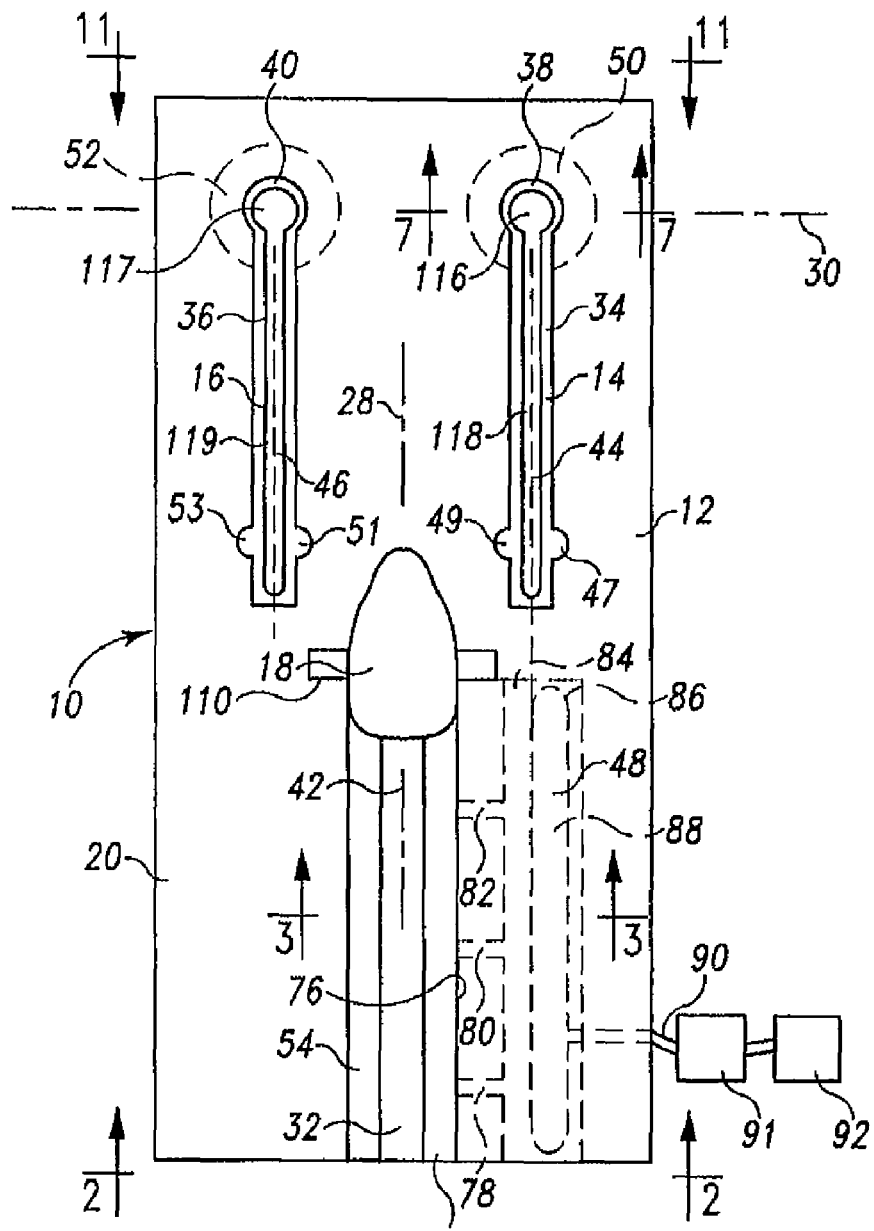
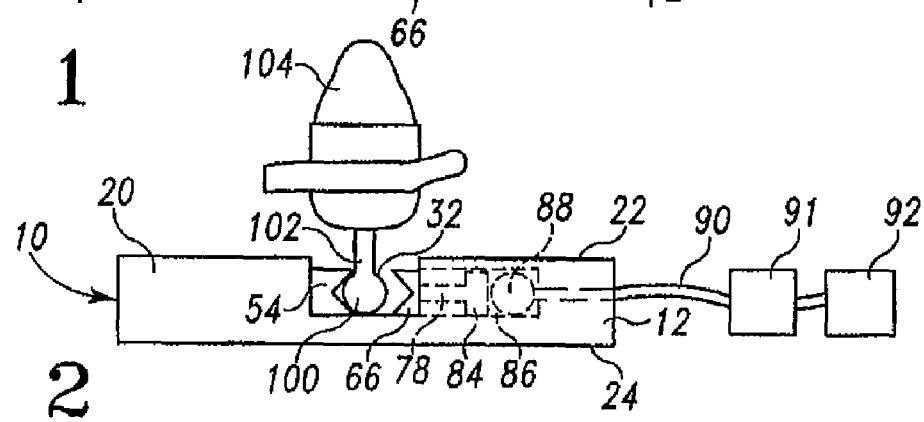
Fig. 1
Fig. 2 ed by applying a tourniquet around the limb, the tourniquet either being integral to the belt or being a separate element wrapped around the limb. In another aspect, the connector is capable of being selectively released to allow the outrigger to be moved with respect to the support belt.

LIMB STABILIZING SYSTEM FOR ARTHROPLASTY

CROSS-REFERENCE TO RELATED APPLICATIONS

This application claims priority to U.S. Prov. App. No. 60/863,694 filed Oct. 31, 2006, entitled "LIMB STABILIZING SYSTEM FOR ARTHROPLASTY," which is incorporated by reference herein in its entirety and to U.S. Prov. App. No. 60/863,711 filed Oct. 31, 2006, entitled "SURGICAL INSTRUMENT SYSTEM WITH BALL AND SOCKET SUPPORT," which is incorporated by reference herein in its entirety.

BACKGROUND OF THE INVENTION

The present invention relates to surgical instruments used during arthroplasty, and more particularly, to a system for stabilizing the position of a patient's leg during knee arthroplasty.

When a skeletal joint is damaged, whether as a result of an accident or illness, a prosthetic replacement of the damaged joint may be necessary to relieve pain and to restore normal use to the joint. Typically the entire joint is replaced by means of a surgical procedure that involves removal of the ends of the corresponding damaged bones and replacement of these ends with prosthetic implants. This replacement of a native joint with a prosthetic joint is referred to as a primary total-joint arthroplasty.

The surgical preparation of the bones during primary total-joint arthroplasty is a complex procedure. A number of bone cuts are made to effect the appropriate placement and orientation of the prosthetic components on the bones. In total knee arthroplasty, the joint gaps in extension and flexion must also be appropriate.

In the case of total knee arthroplasty, cutting guide blocks are used in creating the bone cuts on the proximal tibia and distal femur. The position, alignment and orientation of the cutting blocks are important in ensuring that the bone cuts will result in optimal performance of the prosthetic implant components. Generally, a tibial cutting block is positioned, aligned and oriented so that the cutting guide surface is in the optimal proximal-distal position, posterior slope, and varus-valgus orientation. Depending on the type of prosthetic implant system to be used, one or more cutting blocks are also positioned, aligned and oriented on the distal femur to ensure appropriate positioning of the distal femoral implant component and appropriate joint gaps.

A variety of alignment guides and cutting blocks have been provided in the prior art for use in preparing bone surfaces in primary total-knee arthroplasty, including alignment guides and cutting blocks used in preparing the proximal tibia and distal femur.

Prior art instrument sets with alignment guides include the Specialist® 2 instruments (DePuy Orthopaedics, Inc., Warsaw, Ind.) for use with DePuy Orthopaedics' P.F.C.® Sigma Knee System. The extramedullary tibial alignment guide for this instrument system includes an ankle clamp, a pair of telescoping alignment rods and a cutting block. The ankle clamp is affixed about the patient's ankle, without extending through the patient's soft tissue. Parts of this system are manually adjustable: the proximal-distal position of the cutting block is adjusted by sliding the telescoping rods and then locking the rods in the desired position; posterior slope is set at the ankle by sliding the distal end of the alignment rod in an anterior-posterior direction to thereby pivot the cutting block into the desired orientation; varus-valgus slope is set by pivoting the cutting block so that the alignment guide pivots about a rod at the ankle clamp.

Many of the bone resections made with these prior art instrument systems are made with the patient's knee in flexion. For accuracy of the bone cuts, the patient's flexed leg should be stabilized while the resections are being made. Currently, this stabilization requires operating room personnel to stabilize the leg (such as by holding it in position) while the surgeon is performing the resections. In addition, during the surgery, the surgeon may want to also place the leg in extension to test the implant or implant trial by moving the patient's leg. Accordingly, while it is desirable to stabilize and fix the position of the patient's leg during part of the arthroplasty procedure, it is also desirable to allow the surgeon to move the patient's leg through flexion and extension during part of the procedure.

SUMMARY OF THE INVENTION

The present invention provides a leg stabilizing system that can be used to selectively fix and stabilize the position, alignment and orientation of the patient's leg during resection of the bones of the knee while also allowing the surgeon to move the leg during other parts of the arthroplasty procedure.

In one aspect, the present invention meets these objectives by providing an intraoperative leg stabilizing system for use in knee joint arthroplasty comprising a platform, a pivotable outrigger and a movable brace. The platform has a longitudinal axis and a transverse axis. The pivotable outrigger is mounted to the platform, and is capable of pivoting about a transverse axis to a plurality of orientations defining different angles with respect to the longitudinal axis of the platform. The movable brace is also mounted to the platform. The platform and the movable brace include structures that allow the movable brace to be moved to a plurality of different longitudinal positions on the platform. The system also includes a movable outrigger locking member carried by the platform for locking the outrigger in a desired orientation with respect to the platform and a movable brace locking member carried by the platform for locking the movable brace in a desired longitudinal position.

In another aspect, the present invention meets this objective by providing a surgical system for use in performing total knee arthroplasty comprising a resection guide for performing a resection of one of the bones of the knee, an instrument support structure for positioning the resection guide and an intraoperative leg stabilizing system. The resection guide has a guide path for guiding the path of travel of a cutting instrument. The leg stabilizing system has a platform having a longitudinal axis and a transverse axis. A pivotable outrigger is mounted to the platform, and is capable of pivoting about a transverse axis to a plurality of orientations defining different angles with respect to the longitudinal axis of the platform. A movable outrigger locking member is carried by the platform for locking the outrigger in a desired orientation with respect to the platform. A movable brace is also mounted to the platform. The brace and the platform include structures to allow the brace to be moved to a plurality of different longitudinal positions on the platform. A movable brace locking member is carried by the platform for locking the slidable brace in a desired longitudinal position. The system also includes a support belt sized and shaped to wrap around a portion of the exterior of the limb and a connector for connecting the outrigger to the support belt. The support belt may include an integral tourniquet, or a discrete tourniquet may be used in conjunction with the support belt to limit blood flow to the surgical area and to optimize stabilization around the patient's leg.

BRIEF DESCRIPTION OF THE DRAWINGS

The invention will be better understood by reference to the figures of the drawings wherein like numbers denote like parts throughout and wherein:

FIG. 1 is a top plan view of an embodiment of an intraoperative leg stabilizing system embodying the principles of the present invention;

FIG. 2 is an end view of the intraoperative leg stabilizing system of FIG. 1, taken along line 2-2 of FIG. 1;

DETAILED DESCRIPTION OF THE ILLUSTRATED EMBODIMENTS

Figure 3:
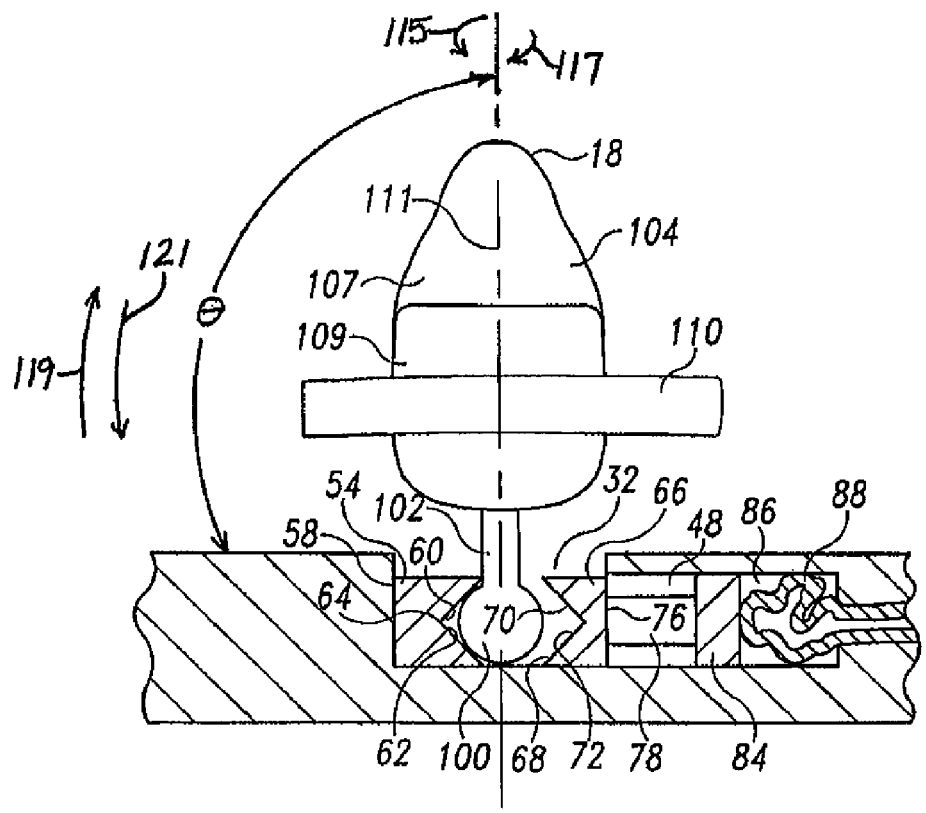
FIG. 3 is an enlarged partial cross-section of the intraoperative leg stabilizing system of FIGS. 1 and 2, taken along line 3-3 of FIG. 1, showing the slidable brace with the brace locking mechanism disengaged.

An embodiment of an intraoperative leg stabilizing system illustrating the principles of the present invention is illustrated at 10 in FIG. 1. The illustrated system is provided for stabilizing and selectively fixing the position of a patient's leg during total knee arthroplasty. The illustrated system includes a platform 12, a pair of outriggers 14, 16 pivotally mounted to the platform 12 and a movable brace 18 mounted to the platform 12. As described in more detail below, the brace 18 is provided to support and position of the patient's ankle, and the outrigger is provided to support and position the patient's thigh. Outrigger locking mechanisms and a brace locking mechanism are also provided so that the patient's leg can be fixed in the desired positions. The brace, and thus the patient's ankle, is movable to a plurality of longitudinal positions on the platform and the brace 18 and the outriggers 14, 16 allow the surgeon to pivot the patient's leg to a desired orientation and degree of flexion, including extension, partial flexion and fully flexed, for example.

The illustrated platform 12 comprises a body 20 with a top surface 22 and a bottom surface 24. The bottom surface 24 is substantially flat so that the platform can be stably supported on a standard operating table (shown at 26 in FIGS. 5-6 and 15-16). The platform may be clamped, bolted, screwed or otherwise selectively fixed to the operating table for stability if desired.

As shown in FIG. 1, the platform 12 has a longitudinal axis 28, a transverse axis 30 and a plurality of openings in the top surface 22. To allow for translational movement of the brace 18, the top surface 22 of the platform is open at a plurality of longitudinally spaced locations. In the illustrated embodiment, the plurality of longitudinally spaced provisions are provided by a first longitudinal groove 32 extending from one end of the platform longitudinally toward the opposite end. Although a groove is desirable in that it allows for infinite longitudinal positioning of the brace, a series of discrete openings could also be used.

Additional openings are provided in the platform to receive the outriggers and to allow for pivotal movement of the outriggers. In the illustrated embodiment, these openings comprise two transversely spaced longitudinal grooves 34, 36 near the opposite end of the platform 12 with enlarged recesses 38, 40 at the ends of the longitudinal grooves 34, 36. The longitudinal axis 42 of the first groove 32 lies between the longitudinal axes 44, 46 of the other two grooves 34, 36. The illustrated platform 12 also includes an elongate chamber 48 running longitudinally along one side of the first groove 32. A pair of chambers 50, 52 surround the recesses 38, 40 at the ends of the longitudinal grooves 34, 36. Short transverse grooves 47, 49, 51, 53 intersect the longitudinal grooves 34, 36 for ease in grasping the outriggers 14, 16 when the outriggers are oriented flat in the grooves 34, 36.

Figure 4:
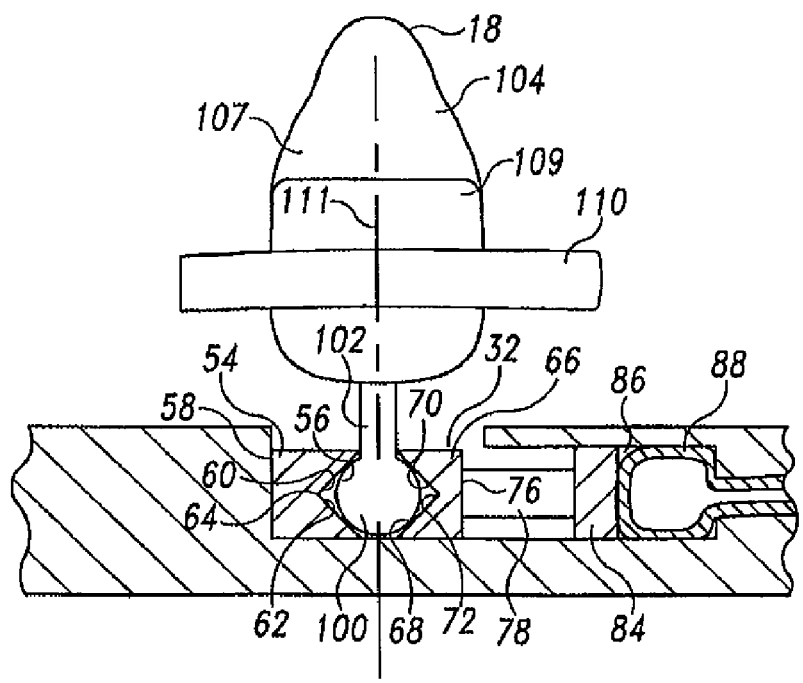
FIG. 4 is a view similar to FIG. 3, showing the slidable brace with the brace locking mechanism engaged to fix the longitudinal position of the slidable brace.

The brace locking mechanism in the illustrated embodiment comprises two elongate rails and an actuator for moving the rail. The platform 12 carries the two elongate rails. One rail 54 is positioned in the first longitudinal groove 32 in the platform and is stationary in the illustrated embodiment. The illustrated first elongate rail 54 runs along substantially the entire length of the first longitudinal groove 32. As best seen in FIGS. 3-4, the first elongate rail 54 has a concave longitudinal surface 56 along the length of one side and a vertical longitudinal surface 58 opposite the concave surface 56. The concave surface 56 is defined in the illustrated embodiment by two faces 60, 62 meeting along an edge 64 running the length of the elongate rail 54.

The second elongate longitudinal rail 66 is spaced from and substantially parallel to the first elongate longitudinal rail 54. The illustrated second rail 66 also runs along substantially the entire length of the first longitudinal groove 32. As best seen in FIGS. 3-4, it has a concave longitudinal surface 68 facing the concave longitudinal surface 56 of the first rail 54. The concave longitudinal surface 68 is defined in the illustrated embodiment by two faces 70, 72 meeting along an edge 74 running the length of the elongate rail 66. The rail 66 also has a vertical longitudinal surface 76 opposite the concave surface 68.

As shown in FIG. 1, a plurality of posts 78, 80, 82 extend outward in a transverse direction from the vertical longitudinal surface 76 of the second elongate longitudinal rail 66 into the elongate rectangular chamber 48 alongside the groove 32. Within the elongate rectangular chamber 48, the posts 78, 80, 82 are connected to an interior straight elongate rail 84. In the illustrated embodiment, the interior straight elongate rail 84 defines a smaller rectangular sub-chamber 86 that holds an expandable diaphragm or bladder 88. The illustrated expandable bladder 88 extends along substantially the entire length of the sub-chamber 86. The expandable diaphragm or bladder 88 is connected through a hose 90 and valve (shown diagrammatically at 91) to a source of compressed air 92.

When the diaphragm or bladder 88 is deflated, the elongate rails 54, 66 are in the positions shown in FIG. 3; when the diaphragm or bladder 88 is inflated, the diaphragm or bladder 88 expands, pushing the rail 84 transversely toward the groove 32, thereby pushing rail 66 further into the groove 32, as shown in FIG. 4. The posts 78, 80, 82 and complementary holes (not shown) in the body 20 of the platform 12 control movement of the rails 66, 84 and maintain substantially transverse linear movement of the rails 66, 84 without any canting. It will be appreciated that other actuators can be used to move the rail 84 between the positions shown in FIGS. 3 and 4, such as a set of mechanical cams and followers, pistons (for example, air operated or pneumatic), solenoid actuators or magnetic actuators, for example.

Within the longitudinal groove 32 adjacent to the stationary elongate rail 54, a substantially spherical portion 100 of the slidable brace 18 is positioned. The substantially spherical portion 100 of the slidable brace 18 is sized and shaped so that when the movable rail 66 is in the position shown in FIG. 3, the brace 18 may be moved back and forth along a linear longitudinal path within the longitudinal groove 32 until a desired position is reached. When the desired position is reached, the elongate diaphragm or bladder 88 may be inflated to push the movable elongate rail 66 against the substantially spherical portion 100 of the brace 18 to fix the brace at the desired position, as shown in FIG. 4.

Figure 10:
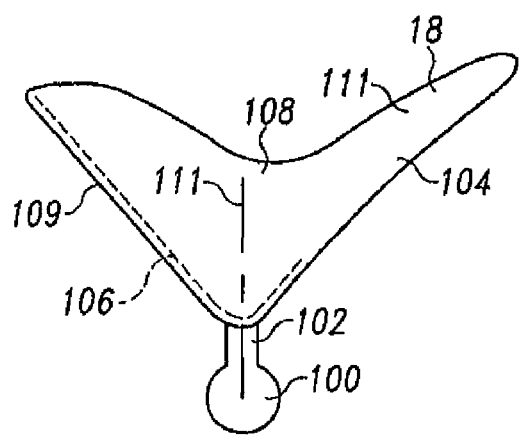
FIG. 10 is a front elevation of an embodiment of a slidable brace for use in the intraoperative leg stabilizing system of the present invention.

The substantially spherical portion 100 of the slidable brace 18 has a unitary post 102 extending upward beyond the top surface 22 of the platform 12. Above the top surface 22 of the platform 12, the post 102 is connected to a support member 104 of the slidable brace 18. The support member 104 is sized and shaped to support a portion of the patient's foot at a desired degree of flexion. It will be appreciated that a variety of materials may be used for the support member 104, and that the support member 104 could comprise an assembly or a body of unitary construction. For example, as shown in FIG. 10, the support member 104 could comprise a base 106 with a body 108 shaped to conform with a portion of the patient's foot and open along an anterior side, with closing or securing members such as straps 110 to hold the patient's foot on the support member 104. A posterior portion of the support member 104 can be sized and shaped to extend proximally beyond the patient's ankle. One or more additional securing members could be provided along the ankle support portion of the body. Alternatively, the support member 104 could comprise a base shaped and sized to support the bottom of the patient's foot at the heel and with a posterior surface shaped and sized to support the posterior surface of the patient's heel, ending distal to the patient's ankle; such an support member is indicated at 104A in FIG. 15 for the brace designated 18A.

Figure 5:
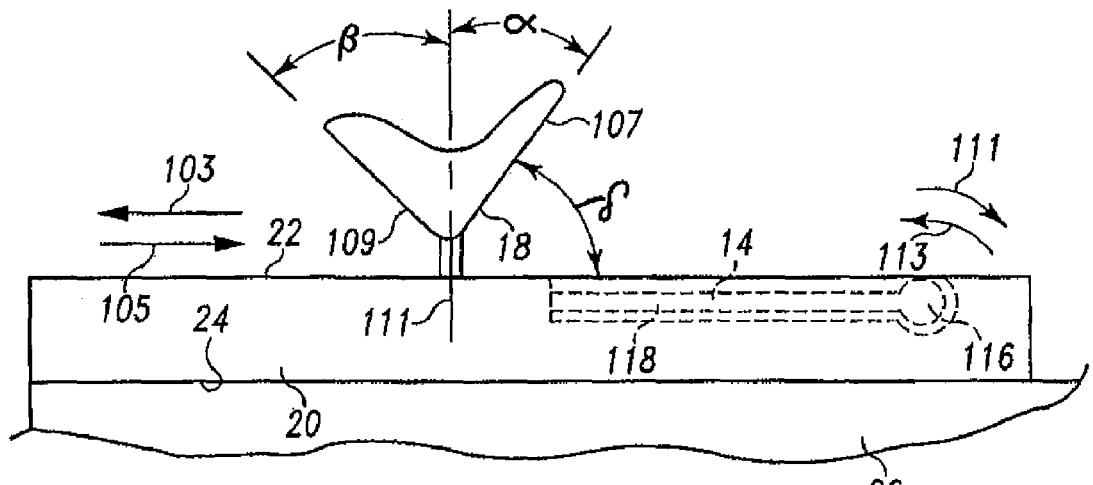
FIG. 5 is a side elevation of the intraoperative leg stabilizing system of FIGS. 1-2, shown with the slidable brace in one longitudinal position and with the outriggers received in slots in the platform.

As shown in FIGS. 5-6, the illustrated support member 104 of the brace 18 includes perpendicular support surfaces 107, 109 that are sized and shaped to support both the distal and posterior surfaces of the patient's heel, and, as indicated above, the posterior support surface 107 may extend below or above the patient's ankle. As illustrated, the distal support surface 109 may be sized and shaped to extend from the patient's heel to toward the toes to support the arch of the patient's foot. As shown in FIG. 5, the illustrated posterior support surface 107 defines an angle α of about 45° with the longitudinal axis 111 of the post 102 and the illustrated distal support surface 109 defines an angle β of about 45° with the longitudinal axis 111 of the post 102.

Figure 6A:
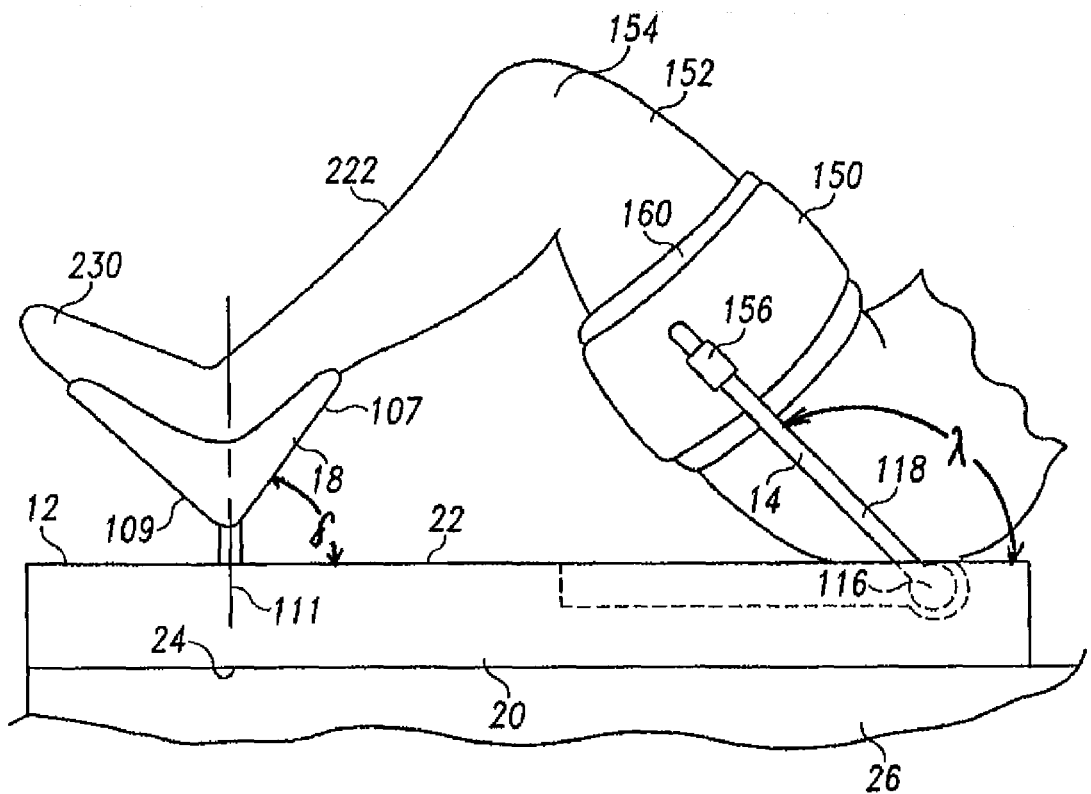
FIG. 6A is a side elevation of the intraoperative leg stabilizing system of FIGS. 1-2 and 5, shown with a patient's foot received in the slidable brace in a longitudinal position and with one of the outriggers pivoted upward and connected to a support belt fixed about the patient's thigh, and with the patient's knee at about 90° flexion.
Figure 6B:
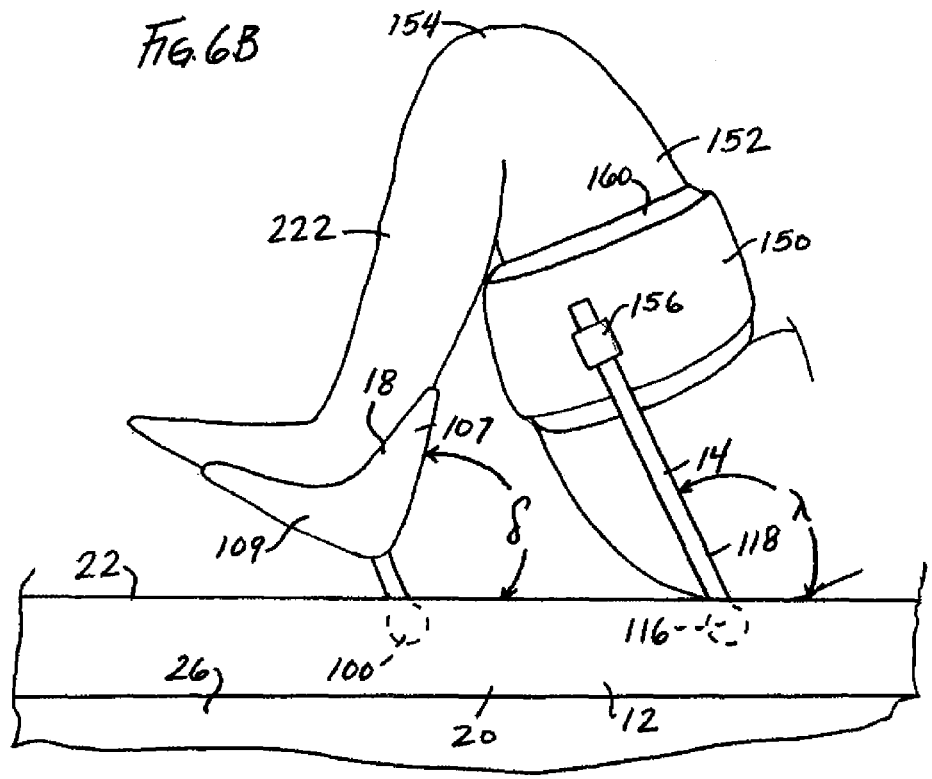
FIG. 6B is a view similar to FIG. 6A, showing the patient's knee in a higher degree of flexion.
Figure 6C:
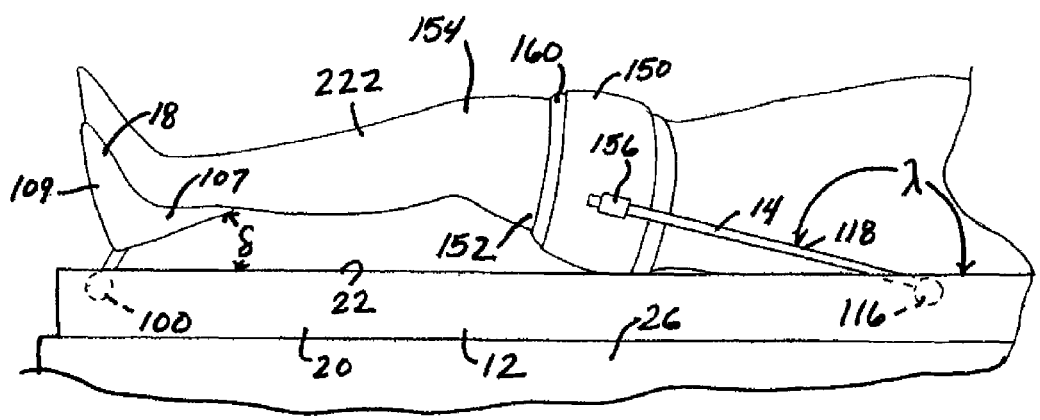
FIG. 6C is a view similar to FIGS. 6A and 6B, showing the patient's knee in extension.

FIGS. 5 and 6 illustrate examples of longitudinal positions possible with the illustrated movable brace 18. Arrows 103, 105 in FIG. 5 illustrate the directions of translational movement for the brace 18. FIGS. 6A, 6B and 6C illustrate some of the possible positions to which the brace 18 can be moved: FIG. 6A illustrates the brace 18 positioned longitudinally so that the patient's leg is at about 90° flexion; FIG. 6B illustrates the brace 18 positioned closer to one end of the platform 12 so that the patient's leg is in deeper flexion; and FIG. 6C illustrates the brace positioned near to the opposite end of the platform so that the patient's leg is in extension. FIGS. 5, 6A, 6B and 6C also illustrate examples of some possible positions to which the outriggers 14, 16 can be pivoted on the platform 12; angular orientations of the outriggers 14, 16 with respect to the top surface 22 of the platform 12 are indicated by the angle λ in FIGS. 6A, 6B and 6C. Arrows 111, 113 in FIG. 5 illustrate the directions of pivotal movement for the outriggers 14, 16. As can be seen from a comparison of FIGS. 5, 6A, 6B and 6C, the outriggers can be pivoted upward from an angle λ of 180° as shown in FIG. 5, to about 160° as shown in FIG. 6C, to about 135° as shown in FIG. 6A, to about 115° as shown in FIG. 6B, as well as to angles of 90° and less and to a multitude of angles of less than 180°.

The brace 18 can also pivot with respect to the platform 12 about multiple axes. The brace 18 can pivot about the central longitudinal axis 111 of the post 102; arrows 115, 117 in FIG. 3 illustrate this degree of rotational freedom of movement. The brace 18 can also be tilted or pivoted about an axis parallel to the longitudinal axis 28 of the platform 12 and through the spherical portion 100 of the brace 18; arrows 119, 121 in FIG. 3 illustrate this degree of rotational freedom of movement. The brace 18 can also be tilted or pivoted about an axis perpendicular to the longitudinal axis 28 of the platform 12 and through the spherical portion 100 of the brace 18; arrows 123, 125 in FIG. 5 illustrate this degree of rotational freedom of movement. Thus, the angular orientations of the posterior support surface 107 and distal support surface 109 of the brace 18 with respect to the plane of the top surface 22 of the platform 12 can be adjusted by pivoting the spherical portion 100: angle δ shown in FIGS. 5, 6A, 6B and 6C may be adjusted to fall above or below 45°; angle θ shown in FIG. 3 may be adjusted to fall above or below 90°; and angle λ shown in FIG. 1 (the angle between the longitudinal axis 127 of the brace 18 and the longitudinal axis of the groove 32) can be adjusted to fall above or below 180°. Together with the translational movement possible, the brace and platform provide substantial freedom for the surgeon to place the patient's leg in a variety of positions during surgery, and to fix the patient's leg in the desired position without requiring hospital staff to manually support the patient's leg.

It should be appreciated that although the brace locking mechanism of the illustrated embodiment utilizes one stationary rail 54 and one movable rail 66, both rails 54, 66 could be movable and a suitable moving and locking mechanism could be provided for both rails 54, 66. Moreover, other structures could be employed as brace locking mechanisms if desired. Although use of the illustrated brace locking mechanism is expected to be advantageous, the present invention is not limited to a particular brace locking mechanism unless expressly called for in the claims.

It should also be appreciated that although the illustrated brace 18 is slidable longitudinally on the platform 12, other structures may be used to mount the brace to the platform and to allow for movement. For example, instead of a groove allowing for sliding the brace, a series of longitudinally spaced sockets could be provided with locking mechanisms. The spaced sockets can be positioned to correspond with standard positions for a knee in flexion and extension, as well as at other desired positions. Use of a longitudinal groove may be desirable to allow for greater flexibility in setting the position of the brace, compared to preset positions available with spaced sockets.

Figure 9:
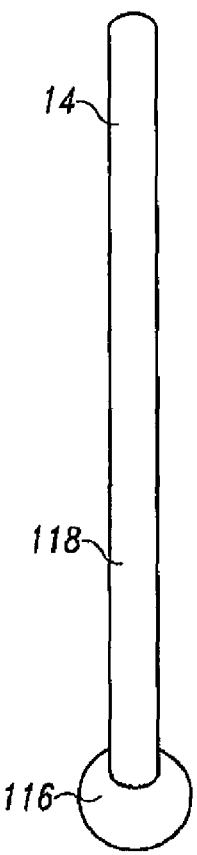
FIG. 9 is a perspective view of a representative outrigger for use in the intraoperative leg stabilizing system of the present invention.

Next considering fixation of the position of the patient's thigh, an example of an outrigger is shown in FIG. 9. It should be understood that the following description of the outrigger 14 applies as well to the outrigger 16. As shown in FIG. 9, the outrigger 14 includes a substantially spherical portion 116 and an elongate stabilizing rod 118 extending outwardly from the spherical portion 116. The central longitudinal axis of the stabilizing rod 118 extends through the center of the spherical portion 116 of the outrigger 14 in the illustrated embodiment. In FIG. 1, the spherical portion of outrigger 16 is designated 117 and the elongate stabilizing rod is designated 119.

As illustrated in FIG. 1, the outrigger 14 is receivable in one of the longitudinal grooves 34 and the outrigger 16 is receivable in the longitudinal groove 36 adjacent to the groove 34. As shown in FIG. 5, the entire outrigger 14 is positioned between the top surface 22 and bottom surface 24 of the platform 12 when the outrigger 14 is in the retracted position. The same holds true for outrigger 16. For use in stabilizing the patient's leg, the outriggers 14, 16 can be pivoted about transverse axis 30 so that the elongate rod portion 118 extends upward above the top surface 22 of the platform 12, defining an angle with the top surface 22 of the platform. For example, the outrigger 14 illustrated in FIG. 6 has been pivoted to a position where the elongate rod portion 118 defines an angle of about 45° with the top surface 22 of the platform.

The illustrated embodiment of the invention allows each outrigger 14, 16 to be locked in a selected orientation with respect to the top surface 22 of the platform 12. As discussed in more detail below, the illustrated embodiment provides a plurality of collets and expandable bladders or diaphragms for locking the outriggers 14, 16 in the selected orientation.

The spherical portions 116, 118 of the outriggers 14, 16 are received within recesses 38, 40 in the platform 12. In the illustrated embodiment, the cylindrical chambers 50, 52 surround these recesses 38, 40. The locking mechanisms associated with each chamber 50, 52 is the same; the locking mechanism associated with chamber 50 and outrigger 14 is described below, but it should be understood that the description applies as well to the chamber 52 and outrigger 16.

Figure 12:
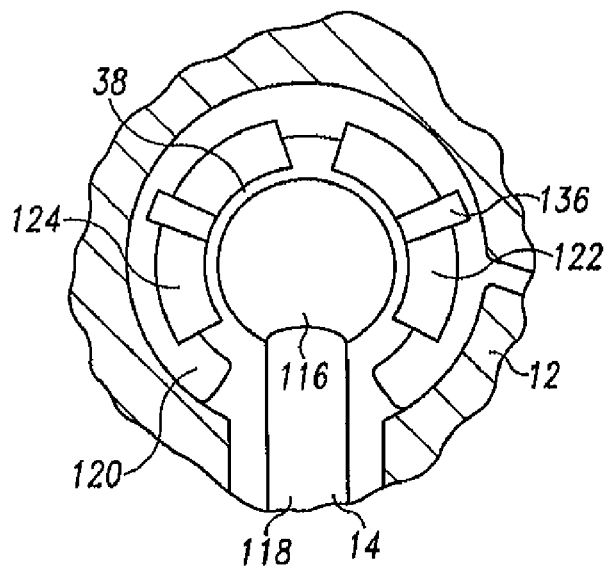
FIG. 12 is an enlarged partial cross-section of the intraoperative leg stabilizing system of FIG. 11, taken along line 12-12 of FIG. 11, showing the outrigger and the outrigger locking system in a disengaged state.
Figure 11:
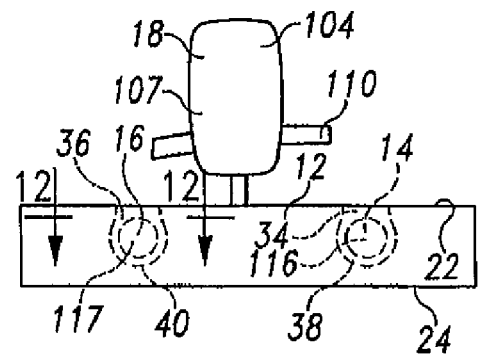
FIG. 11 is an end view of the intraoperative leg stabilizing system of FIG. 1, taken along line 11-11 of FIG. 1.
Figure 14:
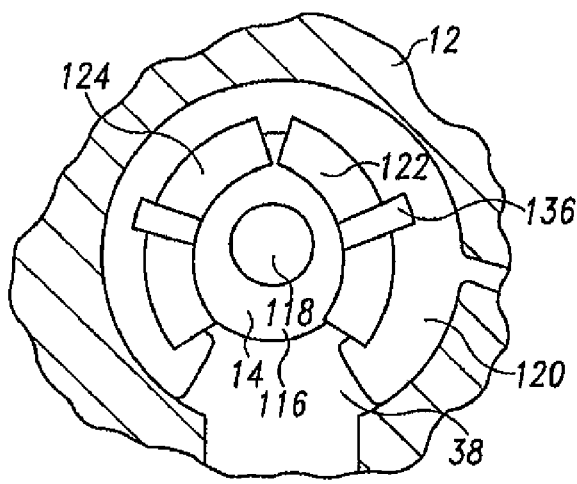
FIG. 14 is an enlarged partial cross-section similar to FIG. 12, showing the outrigger with the outrigger locking system engaged.

As shown in FIGS. 7-8, 12 and 14, the locking mechanism for outrigger 16 includes an expandable substantially toroidal diaphragm or bladder 120 and a pair of collet members 122, 124 received within the chamber 50. The collet members 122, 124 are positioned along the inner diameter of the toroidal diaphragm or bladder 120. As shown in FIGS. 12 and 14, the collet members 122, 124 are curved, defining arc segments.

Figure 13:
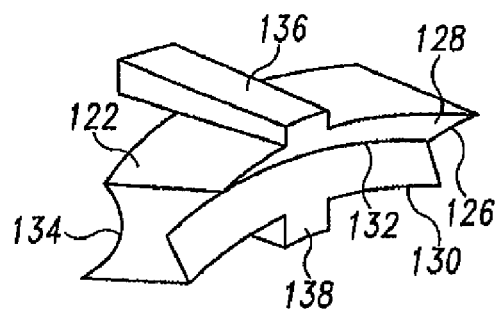
FIG. 13 is a perspective view of one of the collet members of FIG. 12.

A representative collet member is shown at 122 in FIG. 13. It should be understood that the following description applied to both collet members 122, 124. As there shown, the collet member 122 has a concave inner surface 126 (shown at 127 for collet member 124 in FIGS. 7-8), defined in the illustrated embodiment by a pair of angled faces 128, 130 meeting along a curved interface 132. The opposite face 134 (shown at 135 for collet member 124 in FIGS. 7-8) of the collet member 122 is concavely curved, and is shaped to bear against a portion of the expandable bladder 120. The illustrated collet member 122 includes integral guide rail portions 136, 138 (shown at 137 and 139 for collet 124 in FIGS. 7-8) extending above and under the diaphragm or bladder 120 to be received in complementary recesses (not shown) in the body 20 of the platform 12 to guide the path of travel of the collet members 122, 124; it should be understood that the collet members 122, 124 could instead have a recess to receive a rail in the body for guided travel, and that other mechanisms for controlled travel of the collet 122 could be used.

Figure 7:
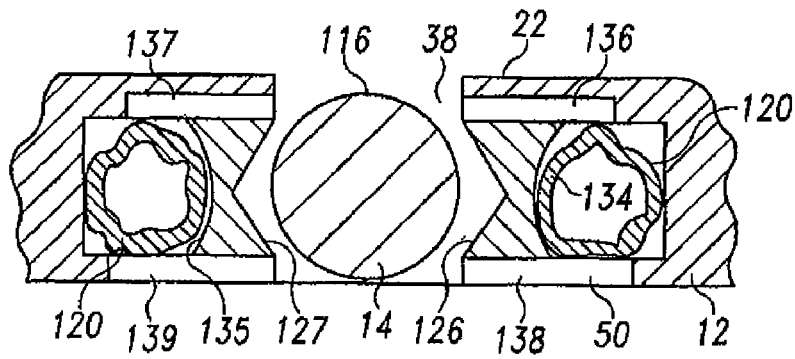
FIG. 7 is an enlarged partial cross-section of the intraoperative leg stabilizing system of FIGS. 1-2 and 5-6, taken along line 7-7 of FIG. 1, showing the spherical portion of one of the outriggers and the outrigger locking mechanism in a disengaged state.

When the expandable diaphragm or bladder 120 is deflated as shown in FIGS. 7 and 12, the collet members 122, 124 are in the positions shown in FIGS. 7 and 12, with the surfaces 126, 127 spaced from the spherical portions 116, 117 of the outriggers 14, 16 so that the outriggers 14, 16 can be pivoted about transverse axis 30 from the position shown in FIG. 5 to the position shown in FIG. 6A, 6B or 6C. For outrigger 14, once the elongate rod portion 118 of the outrigger 14 is pivoted to the desired orientation, such as the orientation shown in FIG. 6, the diaphragm or bladder 120 can be inflated so that it expands, pushing the concave surfaces 126, 127 of the collet members 122, 124 against the spherical portion 116 of the outrigger 14, thereby locking the outrigger 14 in the desired orientation. The rails 136, 137, 138, 139 and complementary grooves maintain substantially radial movement of the collet members 122, 124. The same mechanism can be applied to lock the position of the other outrigger 16. It will be appreciated that the system could allow for separate operation of the locking mechanisms for each outrigger 14, 16, or could allow for simultaneous actuation of the locking mechanisms. It will be also appreciated that other actuators can be used to move the collet members 122, 124 between the locked and unlocked positions, such as a set of mechanical cams and followers, pistons (for example, air operated or pneumatic), solenoid actuators or magnetic actuators, for example. It should also be appreciated that the illustrated collets represent an example of an outrigger locking member; although the illustrated collets are expected to be advantageous, the present invention is not limited to the use of such collets unless expressly called for in the claims.

Figure 8:
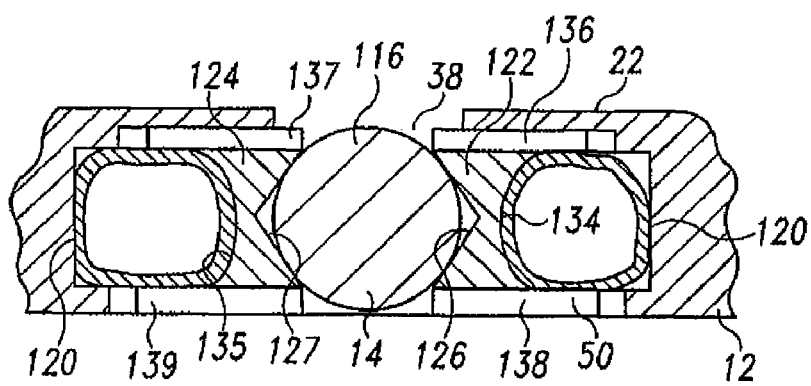
FIG. 8 is a view similar to FIG. 7, showing the outrigger locking mechanism engaged.

The substantially spherical portion 116 of each outrigger and the collet members 122, 124 are sized shaped to allow for pivotal movement of the outrigger when the locking mechanism is disengaged, as in FIGS. 7 and 12, and to provide for locking of the outrigger 16 against pivotal movement when the locking mechanism is engaged, as in FIGS. 8 and 14.

The pneumatic locking system for the outriggers would include suitable hoses connecting the diaphragms or bladders 120 to a source of compressed air through a suitable valve mechanism. Both valve mechanisms may operate to maintain pressure in the bladders 88, 120 until selectively opened by the surgeon (such as through a switch). Maintaining pressure to keep the bladders 88, 120 expanded serves to lock the pneumatic locking mechanisms against the spherical portions 100, 116 of the brace 18 and outrigger 14 (or outrigger 16).

The platform 12, outriggers 14, 16 and slidable brace can be made of any suitable materials for surgical instruments. For example, the platform and outriggers could be made of standard metals, such as stainless steel, or a substantially rigid reinforced polymer or co-polymer. Parts of the slidable brace, such as the post 102 and spherical portion 100 could also be made of standard metals, such as stainless steel, or a rigid reinforced polymer or co-polymer, while the body 108 could be made of a pliable polymer to allow it to be fitted to the patient's foot. The strap 110 could be made of a hook and loop strip (such as a Velcro™ brand fastener, for example), or could comprise a strap with a buckle or snaps for positioning around the body 108 and patient's foot. The rails 54, 66, 84 and collet members 122, 124 could be made of standard metals, such as stainless steel, or of suitable polymers or co-polymers, with or without reinforcement materials. The bladders 88, 120 can be made of suitable polymers or co-polymers. The present invention is not limited to any particular material for any of the components unless expressly called for in the claims.

It should be appreciated that the illustrated pneumatic locking systems for the slidable brace 18 and for the outriggers 14, 16 are provided for purposes of illustration only. A variety of mechanisms could be employed to selectively lock the positions of the slidable brace and the outriggers, such as a set of mechanical cams and followers, pistons (for example, air operated or pneumatic), solenoid actuators or magnetic actuators, for example. The present invention is not limited to any particular brace locking mechanism or outrigger locking mechanism unless expressly called for in the claims.

To fix the outrigger 14 or 16 to the patient's thigh to fix the position and degree of flexion in the patient's leg, the outrigger 14 or 16 is selectively connected to a support belt, band or sleeve 150. The support belt or band (or sleeve) 150 is sized and shaped to wrap transversely around a portion of the patient's thigh (shown at 152 in FIGS. 6 and 15-16) proximal to the knee joint (shown at 154 in FIGS. 6 and 15-16). A connector 156 is attached to the support belt 150. In the illustrated embodiment, the connector 156 comprises a strip with a hook section and a loop section (such as a Velcro™ brand fastener). The connector 156 is sized and shaped to wrap around a portion of the elongate rod portion 118, 119 of the outrigger 14, 16 to stabilize and fix the patient's thigh 152 against the outrigger 14, 16 when the outrigger is raised so that a portion of it is adjacent to the patient's thigh. A suitable support belt 150 for thighs may have an overall length, for example, of about 75-90 cm (about 30-36) inches and a width of about 10-15 cm (about 4-6 inches).

The support belt or band 150 can be made of any suitable material for surgical applications. Suitable materials should be sterilizable, flexible enough to wrap around the patient's limb, substantially inelastic, and sturdy enough for the application described herein. For example, webs of nylon, polypropylene, polyester or other polymers may be suitable, either in the form of single layers or laminates. The material may be reinforced, for example, with fibers or with stays (extending, for example, across with width or shorter dimension of the belt) and the belt may have multiple plies for strength.

It should be understood that all dimensions and materials are identified for purposes of illustration only. The present invention is not limited to any particular dimension or material unless expressly called for in the claims.

In the illustrated system 10, the support belt or band 150 is wrapped transversely around an expandable cuff or tourniquet 160 that is sized and shaped to wrap around a portion of the patient's thigh 152 proximal to the knee joint 154. The expandable cuff 160 may be connected to the source of compressed air 92 through suitable valves (not shown) and switches (not shown). The inflatable cuff 160 can comprise a standard air-tight bladder connected to an air-supply hose. For example, the cuff 160 can be made of materials and constructed similar to standard inflatable blood pressure cuffs. The cuff 160 may include hook and loop strips (such as Velcro™ brand fasteners) so that the cuff can be fixed about the patient's thigh, although other mechanisms (such as buckles or snaps) could be used. Use of such a cuff is advantageous in that it not only optimizes fixation around the patient's leg, but also limits blood flow to the surgical area.

Although in the illustrated system the support belt 150 and expandable cuff 160 are discrete elements, it should be understood that they may comprise a unitary structure. It should also be understood that the support belt 150 of the present invention could comprise other types of structures such as a vacuum immobilizer. A suitable vacuum immobilizer support belt could comprise an elongate air-tight bag or casing of flexible material filled with elastically deformable spherulic beads made of a material such as expanded polystyrene. The bag or casing could include evacuation ports or valves through which air may be evacuated to form vacuums therein. Air would be evacuated after the bag or casing was wrapped around the patient's thigh; evacuation of air would cause the beads to compact together to form fit the patient's thigh and to become rigid in this shape. Examples of devices utilizing such structures include U.S. Pat. No. 6,308,353, U.S. Pat. No. 6,066,107 and U.S. Pat. No. 3,762,404, the disclosures of which are incorporated by reference herein in their entireties.

Figure 15:
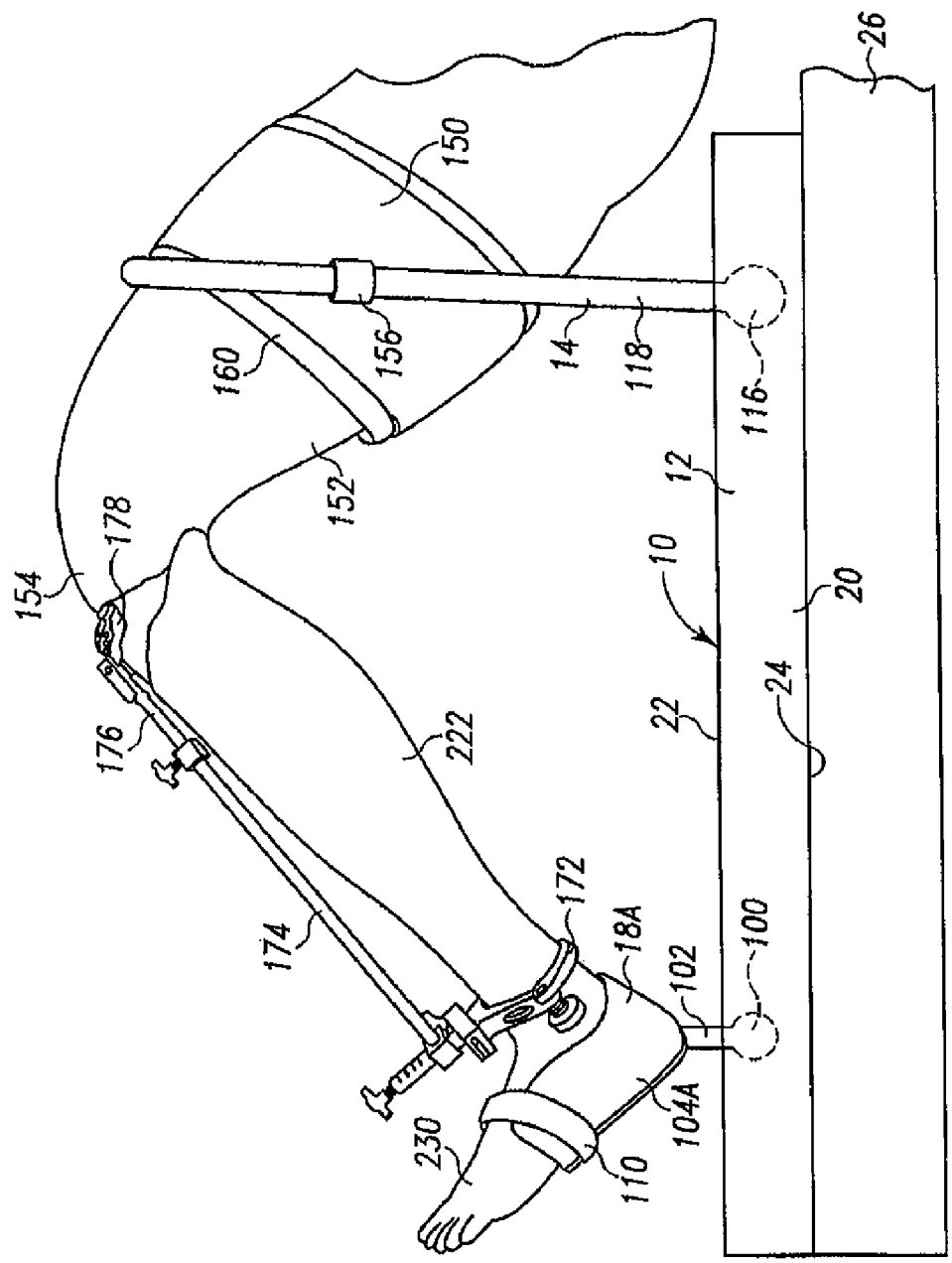
FIG. 15 is a side elevation similar to FIG. 6, showing the intraoperative leg stabilizing system of the present invention in use with parts of one type of surgical instrument system used in knee arthroplasty.

The illustrated intraoperative leg stabilizing system 10 may be used with several different types of systems used to position, align and orient resection guides during knee arthroplasty. FIG. 15 illustrates use of the intraoperative leg stabilizing system 10 with a parts of the commercially available Specialist® 2 instruments (DePuy Orthopaedics, Inc., Warsaw, Ind.), use in implanting DePuy Orthopaedics' P.F.C.® Sigma Knee System. The illustrated extramedullary tibial alignment guide comprises an ankle clamp 172 and a pair of telescoping alignment rods 174, 176 used to position, align and orient a resection guide or cutting block 178. It should be appreciated that the intraoperative leg stabilizing system 10 of the present invention could also be used with commercially available intramedullary instrument systems, and with other commercially available instrument systems.

Figure 16:
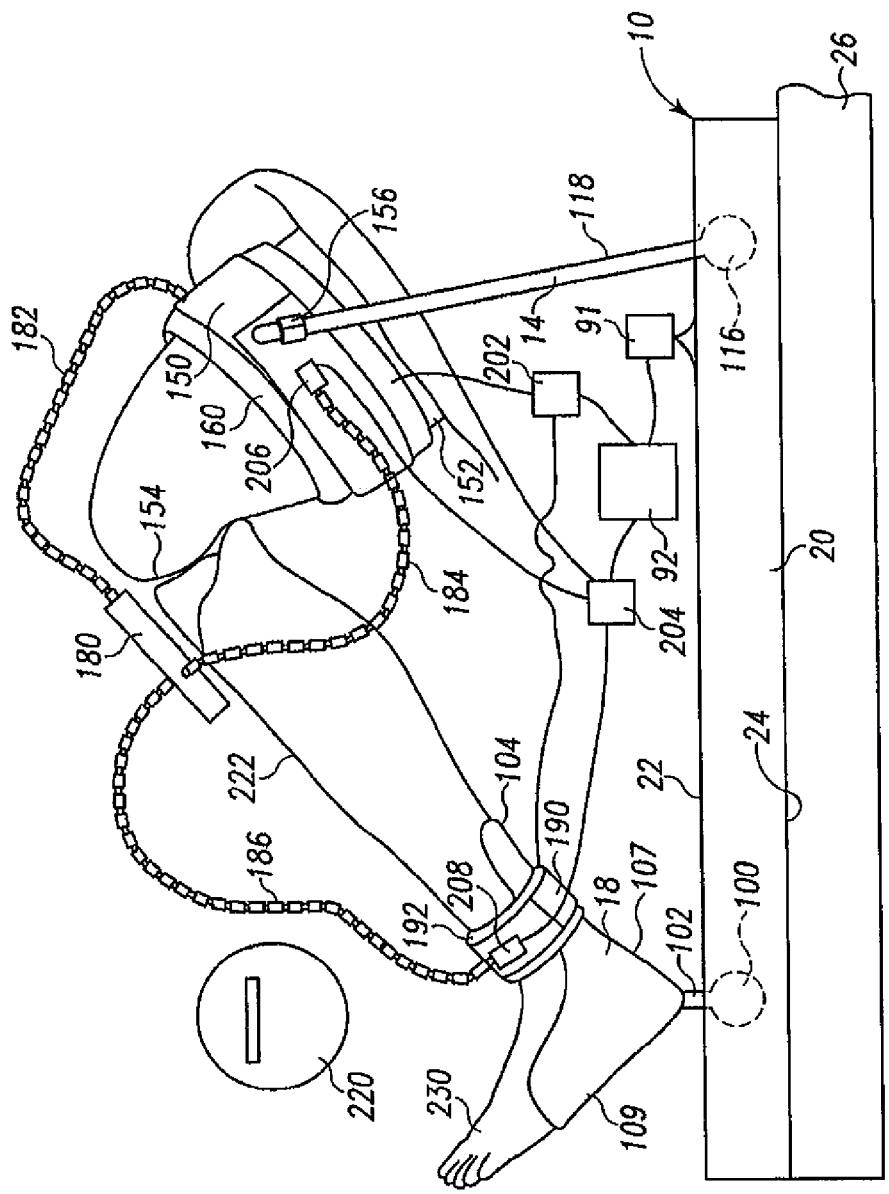
FIG. 16 is a view similar to FIGS. 6 and 15, showing the intraoperative leg stabilizing system in use with parts of another type of surgical instrument system usable in knee arthroplasty.

FIG. 16 illustrates use of the intraoperative leg stabilizing system 10 with parts of the surgical instrument system disclosed in U.S. utility patent application Ser. No. 11/926,892, filed concurrently herewith by Carl F. Livorsi, Joseph G. Wyss, Norman T. Brisebois, Mark A. Capabianco, Michael J. Fortin, Kenneth R. Hayes, James M. Kennedy, John J. McMorrow, Paul J. Monteiro, Jean-Pierre Nuss and Phillip G. Withee, based upon U.S. Provisional Patent Application Ser. No. 60/863,711, which is incorporated herein in its entirety. The instrument system illustrated in FIG. 16 includes an instrument support system comprising an instrument support frame 180 with three ball and socket arms 182, 184, 186. In this embodiment, the support belt or sleeve 150 also serves as a proximal base for the two proximal arms 182, 184 of the instrument support system. The illustrated system also includes a distal base 190 to which the third arm 186 is connected. The distal base 190 surrounds a distal expandable cuff 192 that wraps around a portion of the body 108 of the slidable brace 18. In this embodiment, the source of compressed air 92 is not only connected to supply air through valve 91 to the pneumatic locking mechanisms of the intraoperative leg stabilizing system 10, but also through switches 202, 204 to supply air to the expandable cuffs 160, 192 and to actuators 206, 208 (and a third actuator not shown in FIG. 16) for stiffening the arms 182, 184, 186. The instrument system of FIG. 16 may also include a resection guide such as that shown at 220 to be supported on the support frame 180 or one of the other types of resection guides disclosed in that patent application.

The intraoperative leg stabilizing system 10 of the present invention can also be used with the instrument support system disclosed in U.S. patent application Ser. No. 11/260,454, entitled "SUPPORT FOR LOCATING INSTRUMENT GUIDES," filed on Oct. 27, 2005 by Joseph G. Wyss and Mara C. Holm, which is incorporated by reference herein in its entirety and in the method disclosed in U.S. patent application Ser. No. 11/259,897, entitled "METHOD OF RESECTING BONE," filed on Oct. 27, 2005 by Joseph G. Wyss and Mara C. Holm, which is incorporated by reference herein in its entirety.

It should be understood that although the illustrated embodiment is shown and described with respect to the knee joint and knee arthroplasty, the principles of the present invention may be applied to other joints and other types of arthroplasty as well.

It should also be appreciated that the illustrated intraoperative leg stabilizing system can be used advantageously in computer assisted surgery.

A method of using the illustrated intraoperative leg stabilizing system 10 in surgery is described below.

The platform 12 is placed on the operating table 26 and secured in place using devices such as clamps (not shown). The patient is placed supine on the operating table with the patient's leg 222 extending over the platform 12 and given a satisfactory anesthetic. The leg 222 is prepped and draped in the usual fashion. The patient's foot 230 is placed on the brace 18 and secured to the brace 18 using the strap 110 or the cuff 192 and base 190 of the embodiment of FIG. 16. The brace 18 is slid along groove 32 until the leg 222 is at the desired degree of flexion. One outrigger 14 or both outriggers 14, 16 are pivoted upward about axis 30 until the elongate rod 118 is aligned and oriented adjacent to the connector 156. The pneumatic locking mechanisms may be actuated to move the rail 66 against the spherical portion 100 of the brace 18 and the collet members 122, 124 against the spherical portion 116 of the outrigger 14 to lock the patient's foot 230 in the desired longitudinal position and to set the outrigger at the desired angular orientation. The outrigger may then be connected to the support sleeve or belt 150 to thereby stabilize the position and orientation of the patient's thigh 152. The cuff 160 (whether of the expandable type or the vacuum immobilizer type) may be actuated either before or after connecting the belt 150 to the outrigger 14 to stabilize the position of the portion of the rod 118 at the patient's thigh.

With the patient's leg so stabilized, the surgeon may use standard procedures to position, align and orient the resection guides and perform resections, to evaluate the resections with implant trials and to implant the prosthetic joint components. At any time during the procedure, the surgeon may chose to change the position of the patient's leg 222 by deactivating the locking mechanisms fixing the position and orientation of the brace 18 and outrigger 14. For example, the patient's leg may be placed in extension and moved through flexion with the locking mechanisms deactivated, and at any time the surgeon may elect to activate the locking mechanisms to once again lock the leg in a desired position and degree of flexion.

It should be appreciated that the surgeon may opt to use one of the outriggers 14, 16 alone or may use them in conjunction, in which case the belt 150 could be provided with two connectors such as connector 156.

While only specific embodiments of the invention have been described and shown, it is apparent that various alternatives and modifications can be made thereto. Those skilled in the art will also recognize that certain additions can be made to the illustrative embodiment. It is, therefore, the intention in the appended claims to cover all such alternatives, modifications and additions as may fall within the true scope of the invention.

I claim:

1. An intraoperative leg stabilizing system for use in knee joint arthroplasty comprising:
    a platform having a top surface, a bottom surface spaced from the top surface, a first longitudinal axis, a second longitudinal axis spaced transversely from the first longitudinal axis, and a transverse axis, the platform having a longitudinal groove along the second longitudinal axis;
    a pivotable outrigger mounted to the platform, the outrigger including a substantially spherical portion and an elongate rod portion, the substantially spherical portion and the platform defining a ball joint mounting the outrigger to the platform, the outrigger being capable of pivoting on the substantially spherical portion about the first longitudinal axis and the transverse axis of the platform to a plurality of orientations such that the elongate rod portion defines different angles with respect to the first longitudinal axis and the transverse axis of the platform;
    a movable outrigger locking member carried by the platform for locking the outrigger in a desired orientation with respect to the platform;
    a movable brace mounted to the platform, the movable brace including a substantially spherical portion and a post extending from the substantially spherical portion, the substantially spherical portion of the movable brace being received within the longitudinal groove along the second longitudinal axis and being slidable longitudinally in the longitudinal groove to a plurality of longitudinal positions, the substantially spherical portion and the platform defining a ball joint mounting the movable brace to the platform, the movable brace being pivotable on the substantially spherical portion about at least three axes to a plurality of orientations such that the post defines different angles with respect to the platform, the substantially spherical portion being longitudinally movable with respect to the platform to a plurality of different longitudinal positions along the second longitudinal axis of the platform;
    a movable brace locking member carried by the platform for locking the movable brace in a desired orientation and longitudinal position;
    a support belt sized and shaped to wrap around a portion of the exterior of the leg; and
    a connector for connecting the support belt and the outrigger.

2. The intraoperative leg stabilizing system of claim 1 wherein the movable outrigger locking member comprises a rail movable from a position wherein the rail does not limit pivoting of the substantially spherical portion of the outrigger to a position where the rail limits pivoting of the substantially spherical portion of the outrigger.

3. The intraoperative leg stabilizing system of claim 2 wherein the rail is curved and is movable in a radial direction toward and away from the substantially spherical portion of the outrigger.

4. The intraoperative leg stabilizing system of claim 1 wherein:
the movable outrigger locking member comprises a rail movable between a position wherein the rail does not limit pivoting of the outrigger to a position wherein the rail limits pivoting of the outrigger;
the movable brace locking member comprises a rail movable between a position wherein the rail does not limit movement of the movable brace to a position wherein the rail limits movement of the movable brace;
the platform further comprising an actuator for moving the rail of the movable outrigger locking member and an actuator for moving the rail of the movable brace locking member.

5. The intraoperative leg stabilizing system of claim 4 wherein at least one of the actuators comprises a device selected from the group consisting of:
an inflatable member;
a solenoid; and
a piston.

6. The intraoperative leg stabilizing system of claim 1 wherein the brace locking member comprises a rail movable in a transverse direction toward and away from the substantially spherical portion of the movable brace.

7. The intraoperative leg stabilizing system of claim 1 wherein the connector comprises a strap attached to the support belt.

8. The intraoperative leg stabilizing system of claim 1 wherein the support belt includes an integral inflatable bladder sized and shaped to wrap around a portion of the exterior of the patient's limb.

9. The intraoperative leg stabilizing system of claim 1 further comprising an inflatable cuff sized and shaped to wrap around a portion of the exterior of the leg.

10. The intraoperative leg stabilizing system of claim 1 further comprising a second pivotable outrigger mounted to the platform at a position spaced transversely from the first pivotable outrigger, the second outrigger including a substantially spherical portion and an elongate rod portion, the substantially spherical portion and the platform defining a ball joint mounting the second pivotable outrigger to the platform, the second outrigger being capable of pivoting on the substantially spherical portion about the longitudinal axis and the transverse axis of the platform to a plurality of orientations such that the elongate rod defines different angles with respect to the longitudinal axis and the transverse axis of the platform.

11. The intraoperative leg stabilizing system of claim 1 wherein the stabilizing system is part of a surgical system including a resection guide for performing a resection of one of the bones of the knee, the resection guide including a guide path for guiding the path of a cutting instrument and an instrument support structure for positioning the resection guide.

12. A surgical system for use in performing total knee arthroplasty comprising:
a resection guide for performing a resection of one of the bones of the knee, the resection guide including a guide path for guiding the path of a cutting instrument;
an instrument support structure for positioning the resection guide; and
an intraoperative leg stabilizing system including:
a platform having a top surface, a bottom surface spaced from and parallel to the top surface, a longitudinal axis, a transverse axis, a first longitudinal groove in the top surface and a second longitudinal groove in the top surface, the first longitudinal groove extending to a depth between the top surface and the bottom surface and the second longitudinal groove extending to a depth between the top surface and the bottom surface;
a pivotable outrigger mounted to the platform, the outrigger including a substantially spherical portion and an elongate rod portion, the substantially spherical portion being received in a recess in the platform between the top surface and bottom surface of the platform to define a ball joint mounting the outrigger to the platform, the recess being open to the top surface of the platform and connected to the first longitudinal groove, the outrigger being capable of pivoting on the substantially spherical portion about the longitudinal axis and the transverse axis of the platform to a plurality of orientations such that the elongate rod defines different angles with respect to the longitudinal axis and the transverse axis of the platform, the pivotable outrigger being pivotable to a position wherein the elongate rod portion is received within the first longitudinal groove and is below the top surface of the platform;
a movable outrigger locking member carried by the platform for locking the outrigger in a desired orientation with respect to the platform;
a movable brace mounted to the platform, the movable brace and the platform including structures to allow the movable brace to be moved to a plurality of different longitudinal positions on the platform;
a movable brace locking member carried by the platform for locking the movable brace in a desired longitudinal position;
a support belt sized and shaped to wrap around a portion of the exterior of the leg; and
a connector for connecting the outrigger to the support belt.

13. The surgical system of claim 12 wherein:
the movable brace includes a support member, a post extending outwardly from the support member and a guide member attached to the post opposite the support member, the guide member including a substantially spherical portion received within the second longitudinal groove in the platform, the guide member being slidable longitudinally in the second longitudinal groove to a plurality of longitudinal positions.

14. The surgical system of claim 13 wherein the brace locking member comprises a rail movable in a transverse direction toward and away from the guide member of the movable brace.

15. The surgical system of claim 12 wherein:
the movable outrigger locking member comprises a rail movable between a position wherein the rail does not limit pivoting of the outrigger to a position wherein the rail limits pivoting of the outrigger;
the movable brace locking member comprises a rail movable between a position wherein the rail does not limit movement of the movable brace to a position wherein the rail limits movement of the movable brace;
the platform further comprising an actuator for moving the rail of the movable outrigger locking member and an actuator for moving the rail of the movable brace locking member.

16. The surgical system of claim 15 wherein at least one of the actuators comprises a device selected from the group consisting of:
- an inflatable member;
- a solenoid; and
- a piston.

17. The surgical system of claim 12 wherein the movable outrigger locking member comprises a rail movable from a position wherein the rail does not limit pivoting of the substantially spherical portion of the outrigger to a position where the rail limits pivoting of the substantially spherical portion of the outrigger.

18. The surgical system of claim 12 wherein the support belt includes an integral inflatable bladder sized and shaped to wrap around a portion of the exterior of the patient's leg.

19. The surgical system of claim 12 further comprising an inflatable cuff sized and shaped to wrap around a portion of the exterior of the leg.

20. An intraoperative leg stabilizing system for use in knee joint arthroplasty comprising:
- a platform having a top surface, a bottom surface spaced from the top surface, a first longitudinal axis, a second longitudinal axis spaced transversely from the first longitudinal axis, and a transverse axis, wherein the platform includes a longitudinal groove;
- a pivotable outrigger mounted to the platform, the outrigger including a substantially spherical portion and an elongate rod portion, the substantially spherical portion and the platform defining a ball joint mounting the outrigger to the platform, the outrigger being capable of pivoting on the substantially spherical portion about the first longitudinal axis and the transverse axis of the platform to a plurality of orientations such that the elongate rod portion defines different angles with respect to the first longitudinal axis and the transverse axis of the platform and wherein the outrigger is pivotable to a position wherein at least a substantial part of the elongate rod portion of the outrigger is received in the longitudinal groove of the platform;
- a movable outrigger locking member carried by the platform for locking the outrigger in a desired orientation with respect to the platform;
- a movable brace mounted to the platform, the movable brace including a substantially spherical portion and a post extending from the substantially spherical portion, the substantially spherical portion and the platform defining a ball joint mounting the movable brace to the platform, the movable brace being pivotable on the substantially spherical portion about at least three axes to a plurality of orientations such that the post defines different angles with respect to the platform, the substantially spherical portion being longitudinally movable with respect to the platform to a plurality of different longitudinal positions along the second longitudinal axis of the platform;
- a movable brace locking member carried by the platform for locking the movable brace in a desired orientation and longitudinal position;
- a support belt sized and shaped to wrap around a portion of the exterior of the leg; and a connector for connecting the support belt and the outrigger.

* * * * *